United States Patent
Charles

(10) Patent No.: US 7,668,732 B1
(45) Date of Patent: Feb. 23, 2010

(54) METHOD TO IMPROVE PERSONALIZED CARE AT AN URGENT CARE FACILITY OR A HOSPITAL EMERGENCY DEPARTMENT FACILITY BY CREATING A HIGH-LEVEL OF QUALITY SERVICE

(76) Inventor: Ronald Alan Charles, 8906 Wallington Dr., Houston, TX (US) 77096

( * ) Notice: Subject to any disclaimer, the term of this patent is extended or adjusted under 35 U.S.C. 154(b) by 1329 days.

(21) Appl. No.: 10/863,677

(22) Filed: Jun. 8, 2004

Related U.S. Application Data

(60) Provisional application No. 60/492,482, filed on Aug. 4, 2003.

(51) Int. Cl.
*G06Q 10/00* (2006.01)
*G06Q 50/00* (2006.01)

(52) U.S. Cl. .......................................... 705/2

(58) Field of Classification Search ............... 705/2, 705/8
See application file for complete search history.

(56) References Cited

U.S. PATENT DOCUMENTS

| | | | |
|---|---|---|---|
| 6,345,260 B1 * | 2/2002 | Cummings et al. ............ | 705/8 |
| 2002/0010597 A1 | 1/2002 | Mayer et al. | |
| 2002/0019749 A1 | 2/2002 | Becker et al. | |
| 2002/0026328 A1 | 2/2002 | Westerkamp et al. | |
| 2002/0032580 A1 * | 3/2002 | Hopkins ....................... | 705/2 |
| 2002/0042724 A1 * | 4/2002 | Victor .......................... | 705/2 |
| 2002/0062224 A1 | 5/2002 | Thorsen et al. | |
| 2002/0103680 A1 | 8/2002 | Newman | |
| 2003/0050794 A1 | 3/2003 | Keck | |
| 2003/0208380 A1 | 11/2003 | Honeycutt | |
| 2004/0078220 A1 | 4/2004 | Jackson | |
| 2004/0220829 A1 | 11/2004 | Baharav et al. | |

* cited by examiner

*Primary Examiner*—Gerald J. O'Connor
*Assistant Examiner*—Trang Nguyen
(74) *Attorney, Agent, or Firm*—Buskop Law Group, PC; Wendy Buskop

(57) ABSTRACT

A system for improving personalized care at an urgent care unit by creating a high-level of quality service includes a special care unit in the urgent care unit and a team trained to provide high quality customer care and thereby invoke patient loyalty to the urgent care unit. The urgent care unit has a contract with an association that enables association members to become qualified patients. Qualified patients are provided an indicator to allow the team to accept the qualified patient for treatment. The qualified patients use an interface to request to request a time, the time is confirmed, and an examination ensues within thirty minutes of the time. The team member makes an evaluation to determine whether the patient stays or is transferred to the emergency department. A treatment is devised based on the evaluation.

8 Claims, 1 Drawing Sheet

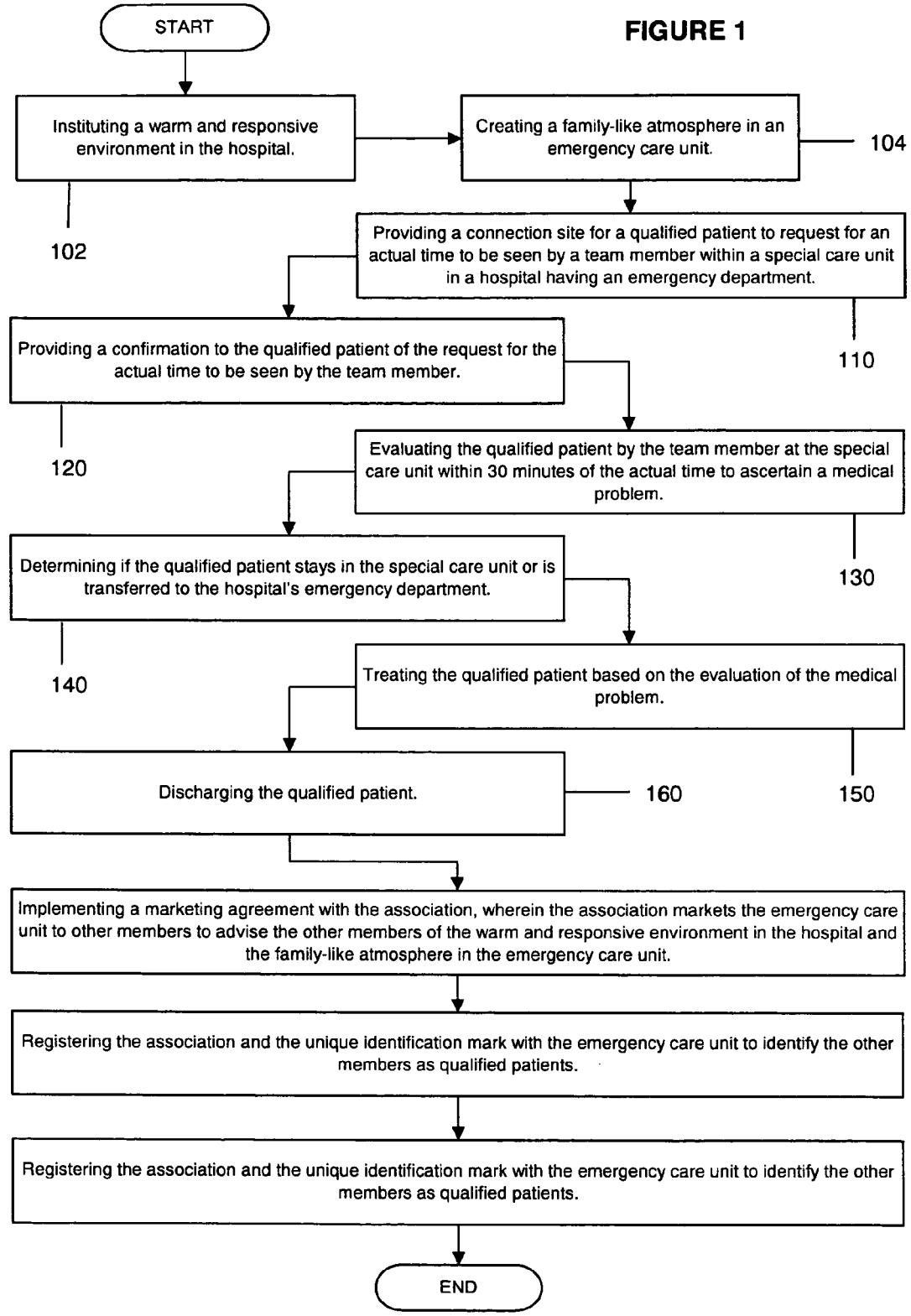

METHOD TO IMPROVE PERSONALIZED CARE AT AN URGENT CARE FACILITY OR A HOSPITAL EMERGENCY DEPARTMENT FACILITY BY CREATING A HIGH-LEVEL OF QUALITY SERVICE

The present application claims priority to U.S. Provisional Patent Application Ser. No. 60/492,482 filed on Aug. 4, 2003.

FIELD

The present embodiments relate to a method for improving personalized care at an urgent care facility by creating a high-level of quality service.

While the present method has nearly universal application within varying departmental urgent care facility environments, a number of features of the present invention are optimized for use within a hospital's Emergency Department facility.

BACKGROUND

The present embodiments relate generally to a process for managing health care and address many of the problems faced today by those involved with health care: payers, patients, and providers. It relates particularly to methods for improving personalized care at hospitals that interface health plan associations who have decided to seek health care services from a doctor and/or some other type of health care provider. These calls are answered by nurses and/or other types of health care professionals, who use the proprietary information tools and processes of the network management system to help patients assess the health needs and then select appropriate care.

The United States ranks first in the world in per-capita health care expenditures. At a time when national health care costs continue to escalate at an alarming rate, managed-care companies and the government have been successful in holding down payments to hospitals; but too often the patient feels unattached from the process. This feeling often leads to a reluctance of patients to seek out the help they need.

Additionally, profit margins of hospitals are decreasing yearly. To survive financially, hospital administrators have been forced to develop novel means of ensuring that the hospital is properly compensated for all services rendered and that patients are treated in manner that encourages them to return to the hospital in times of need. Today, the provision of medical care or personal care for a patient in a hospital often assumes a subordinate role to the extensive amount of information that the hospital requires from the patient. Hospital administrators often need to maintain significant quantities of patient data consisting of information such as admissions, medical history, insurance, and billing. To meet the ever increasing financial demands of providing high quality health care to patient's proper reimbursement from insurance companies is absolutely essential. Complicating the problem is the unique, often hectic, nature of an Emergency Room.

Working under highly stressful conditions, emergency medical team members are routinely forced to forego personalized care in order to balance administrative tasks and treat multiple patients suffering from severe injuries. Often, patients arrive in an Emergency Room with reduced communicative abilities as to their identity, compounded with life threatening injuries that require immediate medical attention. An attending Physician may issue an array of orders ranging from X-rays, administration of medication, and laboratory assays; all of which must be tracked and recorded to insure proper billing and reimbursement. In these situations, it is unacceptable to interfere with the administration of care in order to obtain patient medical care, or resource utilization data. Often when there is interference with the administration of care the patient is ignored as a person and treated as a series of problems. This only adds to anxiety of the patient and increases their feeling of isolation towards the hospital.

A majority of patients initially come to a hospital through the Emergency Room. A patient will inevitably make a decision about using the hospital for future needs, as well as recommending the hospital to others, based on this initial visit and the treatment during that visit. For hospitals to remain viable and competitive, they must make an effort to personalize care in the Emergency Room in order to encourage patients to choose their hospital for future needs.

Furthermore, most patients with insurance obtain their insurance through a membership with an association. Associations can be any group of people from unions to employees of the same company. A need exists for hospitals to implement a marketing agreement with these types of associations. These associations would actively advise their members of the warm and responsive environment in the hospital and the customer friendly atmosphere in the area surrounding the Emergency Room. In return, the hospital would implement a program where a patient belonging to one of these associations would be identified as a qualified patient merely by their membership.

A need exists for a system to improve personalize care at an urgent care facility. This system would allow hospital administrators to optimize utilization of resources, including utilization of medical personnel, such as nurses, and other medical resources, such as beds, medications, and the like. The system will additionally provide the ability to track effectively the efficiency of patient care provision on a personalized level. In a broader sense, this system would allow hospital administrators to monitor the cumulative activity of a given department over a time period and assess staff and administrative efficiency as needed to determine if personalized care is being given and if those patients are returning to the hospital for their future needs.

SUMMARY

A system for improving personalized care at an urgent care facility by creating a high-level of quality service contemplates operating using a special care unit in a hospital having an emergency department. The special care unit comprises at least one examination room, at least one computer, and at least one work area. The special care unit can include additional qualified patient services. The system has a team comprising at least a doctor, nurse, and clerk. The team is used in the special care unit and is trained to provide high quality customer care and thereby invoke patient loyalty.

The system includes a contract between the urgent care facility, the special care unit, and the association for the benefit of the member enabling the member to become a qualified patient, an indicator provided by the association to the qualified patient to allow the team to accept the qualified patient for treatment; and an interface established by the special care unit for the qualified patient to request an actual time to be seen by the team.

The team provides the qualified patient with a confirmation of the actual time to be seen provided by the team. When the qualified patient arrives at the special care unit, an examination is performed by the team on the qualified patient within thirty minutes of the requested time. For the examination, an evaluation is made to determine whether the qualified patient stays in the special care unit or is transferred to the emergency department by the team. Finally, treatment is performed on the qualified patient by the team based on the evaluation by the special care unit. When the treatment is complete, the qualified patient is dispositioned by the team after the treatment.

BRIEF DESCRIPTION OF THE DRAWINGS

The present embodiments will be explained in greater detail with reference to the appended Figures, in which:

FIG. 1 depicts a schematic of an embodied of a system of improving personalized care at an urgent care unit by creating a high-level of quality service.

The present embodiments are detailed below with reference to the listed Figures.

DETAILED DESCRIPTION OF THE PREFERRED EMBODIMENTS

Before explaining the present embodiments in detail, it is to be understood that the embodiments are not limited to the particular embodiments herein and can be practiced or carried out in various ways.

The embodied systems for improving personalized care at an urgent care facility by creating a high-level of quality service are cost effective, save lives, and increase productivity of workers. The system promotes improved health care. This novel system is designed to get injured workers back to work quicker, which, in turn, provides an overall stimulus to the economy.

The system establishes patient loyalty, which is a bond between the patients and the urgent care facility. The established bond encourages patients to return to the same urgent care facility for future medical needs With reference to the Figures, FIG. 1 is a schematic diagram of the system of the improving personalized care at an urgent care unit by creating a high-level of quality service.

The system (5) provides high customer quality by creating an atmosphere of personal value, personal care, personal appreciation, and comfort. The first step in creating this a high-level of customer quality is having the personal information already on-line to facilitate the registration process. Other steps include having a greeter to welcome in-coming patients, having refreshments (including drinks and minor food stuffs) for waiting patients and family members, and having a waiting area with comfortable seating, music, and appropriate reading material. The waiting area can have computer ports or computer stations for on-line access by the waiting patients. The customer friendly environment can include services for watching young children.

Other steps include a specially trained team focused to dealing with the individual problems of each patient and the concerns of the family members. The customer friendly environment includes systems for the qualified patients to more easily obtain prescriptions. Another goal of the customer friendly environment is to create an atmosphere with a process for the efficient handling of history, patient evaluation, necessary "paperwork", and disposition of the patient for further care or tests.

The system includes a special care unit (10) in an urgent care facility (15) or in a hospital with an emergency department. The special care unit comprises at least one examination room (20), at least one computer (25), and at least one work area (30). The special care unit can have additional qualified patient services (35) including a welcome area, refreshments, a waiting area, computer access, internet access, child watching services, and combinations of these services.

The team member is part of a qualified team (40). The qualified team is developed for use in a designated urgent care facility or hospital, especially hospitals with emergency rooms. The team operates in an area near or adjacent to the emergency room. These areas are known as "Special Care Units". The "Special Care Units" are designed to allow the qualified team to handle the qualified patients with the need for only minimal emergency room equipment. Software on the computer allows for scheduling of qualified patients, production of reports for patient charts, an interface with hospital, urgent care facilities, or other medical facility databases to download patient histories. The scheduling software provides an indication of the availability of when a patient can be seen by the team.

The examining rooms in the "Special Care Units" are typical rooms, with an otoscope, opthamology instruments, examining tables, chairs, sinks, other tables, scalpels, and other medical supplies, such as needles, gauze, and suture materials. The examining rooms include certain medications including pain medications and antiseptics for cleaning wounds. The work area provides an area where paperwork can be handled and where the computer and an Internet connection can be located.

The system includes a team (40) used in the special care unit (10). The team (40) is optimally at least a doctor, nurse, and a clerk. The team (40) is trained to provide high quality customer care and thereby invoke hospital loyalty or loyalty to the urgent care facility. The training involves instruction in the following skills: listening skills; patient psychology; general customer service skills; oral and written communication skills; team building skills; time management skills; and combinations of these skills. The team (40) can have special training, reading materials, tests, and evaluations to insure a high level of customer service in the special care unit. The system contemplates that periodic reviews of the level of care can occur by methods such as comment cards and spot inspections.

The system contemplates that the team member is a person qualified to handle the needs of the qualified patient. Preferably, the team (40) can include additional clerks, nurses, nurse practitioners, additional physicians, physician assistants, and combinations thereof. Additionally, a team (40) could include a clerical member, trained to handle accounting, billing or other clerical tasks.

The system includes an association (45) having at least one member (50a and 50b). The system contemplates that the association (45) incorporates a group of people associated with one another through a health plan. Types of associations (45) contemplated by the system include unions, government agencies, emergency medical services, police associations, fire fighter groups, employee groups, human resource departments of companies, teacher associations, and retired person associations. An association (45) can be an organization of numerous members from a defined region.

The system includes a contract (55) between the hospital or alternatively the urgent care facility, which can be a doctor's office and the special care unit, and the association. The contract (55) is a binding agreement between the parties for the benefit of the members of the association. Through the contract, the members become qualified patients (60). The agreement covers the cooperation between the association and the management group of the special care unit work to together to market the special care unit to potential qualified patients. It is noted that the urgent care facility can be a hospital with an emergency department, or another facility which is open at non-regular business hours for patients to get acute or urgent care without a specified appointment time. It should be noted that a doctor's office can operate as an acute care facility.

The association and the special care units shall notify the potential qualified patients of the locations of the special care units; the hours of available service of the special care units; the phone number of the special care units or a scheduling service; the web site address of the special care units; an information center to answers questions about the special care units; and other pertinent information needed to have the potential qualified patients easily access the special care units.

The system contemplates that the association and the management group accomplish the task of marketing the special care units by sending newsletters, organizing meetings, sending e-mail, sending direct mailings, advertising, and combinations thereof. Examples of advertising include stickers, magnets, promotional items, and other similar tokens used to market the special care units. The associations advise the members of the on a regular basis, but at least monthly as a minimum.

The association provides each qualified patient with an indicator (65). The indicator (65) allows the team to accept the qualified patient for treatment. The association (45) and the indicator (65) are registered with the special care unit to identify other members as qualified patients. The association (45) attempts to provide appropriate insurance information to the special care units so the care of the qualified patient can be expedited. The association informs the qualified patient that they should mention the special care unit when they present to the emergency department triage for treatment.

The system operates for individuals who are referred to hereafter as qualified patients (60). Qualified patients (60) are individuals who have contracted for specialized care from a qualified team of health professionals through an association. A qualified patient (60), as an individual, can be a union member, police officer, hospitality industry member, hospital employee, emergency medical services member, governmental worker, or other workers identified by a uniform. The qualified patient (60) can belong to a union or can be an employee of a corporation that is visually identified, such as by a sticker with an employee logo, by an employee badge, or by a corporation issued smart card.

Family members with insurance are be qualified patients under this system. A family member is a spouse, a dependant, or other specially designated persons of the primary insured. Specially designated persons include grandparents, life partners, foster children, dependent aunt, dependent uncles, and siblings.

The special care unit (10) establishes an interface (70). The interface (70) allows the qualified patient to request an actual time to be seen by the team. The actual time requested by the qualified patient is a defined, specific time, such as 9:15 am. The qualified patient may request any hour of the day that is not already requested by another qualified patient and during which the special care unit is open. It is initially contemplated that the special care unit can be open for 10 to 12 hour shifts and possibly for 24/7 shifts (24 hours, 7 days a week). The team member is preferably seen within a 30 minute window around the actual specific time by the qualified patient. If the qualified patient misses this preferred 30 minute window, it is contemplated, that there is an optional increase in the amount of the co-pay by an amount of a penalty, if the qualified patient does not show up. It is contemplated that up to $40 of penalty could be assessed against a late arriving or non-arriving patient.

In the system, the qualified patient requests an actual time (75) to be seen by a team member within a special care unit in an urgent care facility, or in a doctor's office, or a hospital having an emergency department. The system contemplates that the team member is a person qualified to handle the needs of the qualified patient. If the need is medical in nature, the team member is a nurse, nurse practitioner, physician, physician assistant, and combinations thereof. If the need is a question concerning billing or scheduling or other clerical task, the team member is a clerk, nurse, nurse practitioner, or other such person in a position to be of qualified assistance.

The qualified patient can communicate with the team using an on-line query service or a telecommunication device. Usable devices include cell phones, satellite phones, or landline phones. The qualified patient can contact the team member using a pager, PDA, or a phone and PDA combination. Other systems include access through an internet website or by mail service. Any one or a combination of these manners to communicate can be used.

The special care unit through the team can give a confirmation (80) to the qualified patient of the actual time (75) to be seen provided by the team. The confirmation (80) of the request for the actual time to be seen by the team member can be completed by a verbal confirmation, e-mail confirmation, confirmation by pager, confirmation by written letter (which is faxed), and combinations thereof. Any of the communication systems used by the qualified patient to communicate with the team member can be used by the team member to confirm the request for the scheduled actual time.

When the qualified patient arrives to the special care unit for the actual appointment time, the qualified patient's "paperwork" is expedited because of the information provided by the association. The indicator on the qualified patient triggers this expedited acceptance.

The system contemplates that bedside registration for the qualified patient is possible when there available services.

The qualified patient is then examined by the team. The examination (85) occurs within thirty minutes of the actual time and making an evaluation.

From the examination (85), an evaluation (90) is made to determine whether the qualified patient stays in the special care unit or is transferred to the emergency department by the team. The evaluation (90) is made by the team. The evaluation (90) involves a physical examination, taking of the patient's history and ordering any necessary tests.

If the qualified patient is transferred to a hospital's emergency department, the team can contact the emergency department and advise of the need to transfer the patient to the emergency department (95). The patient can then be physically moved to the higher level of care area in the emergency department (95) from the special team unit.

If the qualified patient stays in the special care unit in the special care unit, treatment (100) is performed on the qualified patient by the team. Treatment (100) of qualified patient can include ordering a test, such as a blood test, urine test, radiological test, cardiac test, stool test, and combinations thereof. The system contemplates that any test and treating procedures normal to emergency rooms can be used with this system.

If transfer is not required, treatment (100) of the qualified patient can include writing a prescription and contacting a contracted pharmacy for expedited filling of the prescription for patient pickup.

The embodied systems contemplate that all information on the patient, the evaluation, and the diagnosis can be completed by using electronic charting, electronic time slotting, and electronic reporting. These types of electronic programs are widely known throughout the medical industry. An example of such as electronic system is T-System medical records system.

The contracted pharmacy can be a 24 hour pharmacy that is near the special care unit. This pharmacy can have a separate contract with trained pharmacists who are adept to quickly filling prescriptions and have the filled prescriptions available to the qualified patient when they arrive at the pharmacy. The contracted pharmacy can have not only increased volume, but increase revenue due to this specially contracted service. The expedited filling of the prescription for patient pickup can be completed by written, electronic, or verbal communication.

One of the goals of this system is to provide good customer service from valet to reserved parking to personalized care to expedite pharmacy prescription pick-up.

After treatment, the qualified patient is dispositioned. Dispositioning means discharging from the special care unit, or the hospital, or transferring the patient to another area of the hospital, and transferring the patient to a clinic, nursing home, assisted-care unit, or to another facility for testing. After the patient is dispositioned, the qualified patient can arrange a follow-up appointment with another physician on the insurance plan in the hospital system, in the same manner as the original appointment was made.

As an alternative, the qualified patient can request that the team provide the qualified patient's employer or a second physician with treatment information. The system contemplates that the physician or other team member can use a cell phone with camera system, such as the ones made by Sony or Ericsson, to photograph and e-mail the patient situation to a private physician, such as showing the physician an abscess.

The system contemplates that the treatment (100) the qualified patient receives coupled with the care from the special care unit can invoke hospital loyalty. The hospital loyalty ensures that the qualified patient can return (105) to the hospital for future care and, thereby, increasing revenue for the hospital and good feelings for the hospital staff.

The systems contemplate that all information on the patient, the evaluation, and the diagnosis can be completed by using electronic charting, electronic time slotting, and electronic reporting. These types of electronic programs are widely known throughout the medical industry. An example of such electronic system is the T-System, which is a form of a template medical records system available for use on a laptop or tablet or PDA.

Tablet PC's can be used by the team members to draw important information about the condition of the patient. Other types of usable electronic devices include voice recognition, special phone services or template medical record systems.

While these embodiments have been described with emphasis on the preferred embodiments, it should be understood that within the scope of the appended claims the embodiments might be practiced other than as specifically described herein.

What is claimed is:

1. A method for improving personalized care within an urgent care unit, a hospital emergency department facility or combinations thereof, by creating a high-level of quality service comprising:

a. creating a special care unit in an urgent care unit, a hospital emergency department facility, or combinations thereof, wherein the special care unit comprises at least one examination room, at least one computer, and at least one work area, and wherein the special care unit further provides services comprising providing a welcome area, providing refreshments, providing a waiting area, providing computer access, providing internet access, providing child watching services, providing scheduling services for providing an actual time for an examination, providing the examination, providing an evaluation, providing treatment, providing dispositioning of a qualified patient to a higher level of care area in the urgent care unit or the hospital emergency department facility, and combinations thereof;

b. providing services with a team comprising at least a doctor, nurse and a clerk and wherein the team provides care and treatment in the special care unit and wherein the team is trained in the following arts:
  i. listening skills;
  ii. patient psychology;
  iii. customer service skills;
  iv. oral and written communication skills;
  v. team building skills; and
  vi. time management skills;

c. enabling an association to issue an indicator for use with the urgent care unit or the hospital emergency department facility, the special care unit, and the association, enabling the member to become a qualified; wherein the association comprises at least one member selected from the group consisting of a union, government agency, emergency medical service group, police group, fire fighter group, employee group, human resource department of a corporation, teacher association, a retired person association, and combinations thereof; wherein the indicator allows the team to accept the qualified patient for treatment; wherein the indicator is selected from the group consisting of a uniform, association identification badge, association trademark, sticker with an unique identification mark, corporation issued smart card, and combinations thereof;

d. requesting an actual time to be seen by the team using an interface established by the special care unit for the qualified patient;

e. sending a confirmation of the actual time to the qualified patient to be seen by the team, and wherein the confirmation comprises a verbal confirmation, email confirmation, confirmation by pager, confirmation by written letter, and combinations thereof; and producing reports for patient charts, and for communicating with medical databases for downloading patient histories by means of software on the computer;

f. performing an examination by the team on the qualified patient, wherein the examination occurs within thirty minutes of the actual time;

g. generating the evaluation of the examination to determine whether the qualified patient stays in the special care unit or is transferred to the higher level of care area in the urgent care unit or the hospital emergency department facility by the team and wherein the evaluation is completed by the team; moving the patient to the higher level of care area in the urgent care unit or the hospital emergency department facility; and h. providing a treatment of the qualified patient by the team based on the evaluation, and wherein the qualified patient is dispositioned by the team after the treatment.

2. The method of claim 1, wherein the qualified patient further comprises a family member of the member.

3. The method of claim 2, wherein the family member is a member selected from the group consisting of a spouse, at least one dependent, a specially designated person, and combinations thereof.

4. The method of claim 1, wherein the team further comprises at least a two clerks, at least two nurses, at least one nurse practitioner, at least two doctors, at least one nurse physician's assistant, and combinations thereof.

5. The method of claim 1, wherein the interface is selected from the group consisting of a website, telephone service, telephone operator, pager, letter, and combinations thereof.

6. The method of claim 1, further comprising enabling the member to receive expedited care in a pharmacy; wherein the expedited care in the pharmacy consists of expedited filling of prescriptions, valet service at the pharmacy, reserved parking at the pharmacy, or combinations thereof.

7. The method of claim 1, further comprising a follow-up appointment, wherein the team arranges the follow-up appointment.

8. The method of claim 1, wherein the team provides a second physician with treatment information at the request of the qualified patient.

* * * * *